United States Patent [19]

Schumann

[11] Patent Number: Plant 6,073

[45] Date of Patent: Dec. 29, 1987

[54] GERANIUM PLANT NAMED TUTTI-FRUTTI

[75] Inventor: Ingeborg Schumann, Bad Ems, Fed. Rep. of Germany

[73] Assignee: Fischer Geraniums, Inc., Curacao, Netherlands Antilles

[21] Appl. No.: 761,096

[22] Filed: Jul. 31, 1985

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A geranium plant named Tutti-Frutti having light rose flower color; double flower form; early flowering and excellent flower production; good chlorophyll quality for transportation; fast rooting; excellent temperature tolerance; compact growth habit; and large flowerhead.

1 Drawing Figure

The present invention comprises a new and distinct cultivar of geranium, botanically known as *Pelargonium zonale*, and hereinafter referred to by the cultivar name Tutti-Frutti.

Tutti-Frutti is a product of a planned breeding program which had the objective of creating new geranium cultivars having light rose flower color, double flower form, compact growth habit, good rooting, temperature tolerance, and good chlorophyll quality for transportation.

Tutti-Frutti was originated from a hybridization made by Ingeborg Schumann in a controlled breeding program in Hillscheid, Federal Republic of Germany in 1981. The female parent was an inbred line from Regina, a popular cultivar in England with double flowers. The male parent of Tutti-Frutti was Hönnefrühling having single light rose flowers, but inferior rooting and growth habit. Both parents are unpatented.

Tutti-Frutti was discovered and selected as one flowering plant within the progeny of the stated cross by Ingeborg Schumann on Aug. 8, 1982 in a controlled environment in Hillscheid, Federal Republic of Germany.

The first act of asexual reproduction of Tutti-Frutti was accomplished when vegetative cuttings were taken from the initial selection in January of 1983 in a controlled environment in Hillscheid, Federal Republic of Germany by a technician working under formulations established and supervised by Ingeborg Schumann. Horticultural examination of selected units initiated in the spring of 1983 and 1984 has demonstrated that the combination of characteristics as herein disclosed for Tutti-Frutti are firmly fixed and are retained through successive generations of asexual reproduction.

Tutti-Frutti has not been observed under all possible environmental conditions. The phenotype may vary significantly with variations in environment such as temperature, light intensity, and day length. The following observations, measurements and comparisons describe plants grown in Hillscheid, Federal Republic of Germany, under conditions which approximate those generally used in commercial practice.

The following traits have been repeatedly observed and are determined to be basic characteristics of Tutti-Frutti, which in combination distinguish this geranium as a new and distinct cultivar.

1. Light rose flower color.
2. Double flower form.

3. Good chlorophyll quality for transportation.
4. Fast rooting.
5. Excellent temperature tolerance.
6. Compact growth habit.
7. Large umbel or flowerhead.
8. Early flowering and excellent production.

Of the many commercial cultivars known to the present inventor, the most similar in comparison to Tutti-Frutti is Schöne Helena, disclosed in U.S. Plant Pat. No. 5,374. Reference is made to attached Chart A which compares certain characteristics of Tutti-Frutti to those same characteristics of Schöne Helena. In comparison to Schöne Helena, Tutti-Frutti has a more compact growth habit, a lighter rose flower color, and an earlier flowering response.

The accompanying color photographic drawing shows typical flower and foliage characteristics of Tutti-Frutti, with colors being as true as possible with illustrations of this type.

Sheet 1 is a color photograph showing Tutti-Frutti in perspective view.

In the following description color references are made to The Royal Horticultural Society Color Chart The color values were determined between 9:00 a.m. and 10:00 a.m. on May 20, 1985 under 30,000 Lux light intensity at Hillscheid, Federal Republic of Germany.

Classification:

*Botanical.*—A hybrid of the genus *Pelargonium l'hert* and species *Pelargonium zonale.*

*Commercial.*—Tutti-Frutti.

INFLORESCENCE

A. Umbel:

*Average diameter.*—128 mm.

*Average depth.*—79 mm.

*Peduncle length.*—126 mm.

*Pedicel length.*—30 mm.

B. Corolla:

*Average diameter.*—44 mm.

*Form.*—Double.

*Color (general tonality from a distance of three meters).*—Pink. Upper surface: mainly 69C; outside whiter, approximately 69D; center of petals darker, approximately 69B.

C. Bud:

*Shape.*—Round to oval.

*Color.*—Yellow-white to slight pink.

D. Reproductive organs:
*Androecium.*—3–8 anthers; stamens.
*Gynoecium.*—4–5 lobed stigma.

E. Spring flowering response period: In Hillscheid, Federal Republic of Germany, in 1983, 65% of plants opened with at least one flower 13 weeks after planting of unrooted cuttings.

F. Outdoor flower production: The total flower count in 1983 in Hillscheid, Federal Republic of Germany, was between 40 and 45 flowers per plant for the June through October observation period.

G. Durability: Shatter resistance very good.

PLANT

A. Foliage:
*Form.*—Kidney shaped.
*Margin.*—Generally round; slightly crenate.
*Color.*—Upper surface: Medium to dark green, 137B. Zonation: Medium zonation.
*Tolerance of botrytis.*—Good.

B. General appearance and form:
*Internode length.*—23 mm.

*Branching pattern.*—An average of 3.9 branches per plant are produced.
*Height.*—210 mm.

CHART A

| CULTIVAR | HABIT | COLOR | UMBEL | EARLY FLOWER RESPONSE (% of plants in-flower after 13 weeks) |
|---|---|---|---|---|
| Schone Helena | Medium | Light Rose | Medium | 40% |
| Tutti-Frutti | Compact | Porcelain Rose, 69C | Large | 65% |

I claim:

1. A new and distinct cultivar of geranium named Tutti-Frutti, as described and illustrated, and particularly characterized by its light rose flower color; double flower form; early flowering and excellent flower production; good chlorophyll quality for transportation; fast rooting; excellent temperature tolerance; compact growth habit; and large flowerhead.

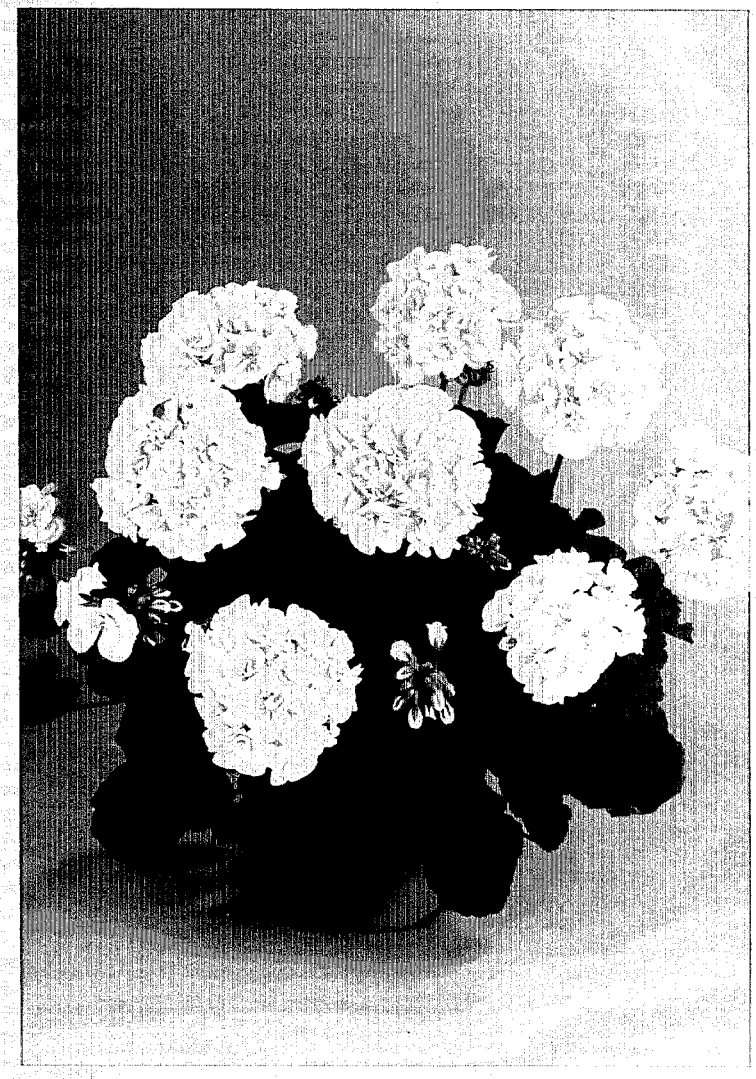

* * * * *